(12) United States Patent
Salopuro et al.

(10) Patent No.: US 8,515,151 B2
(45) Date of Patent: Aug. 20, 2013

(54) GENERATION OF FREQUENCY DISTRIBUTION FOR OBJECTS

(75) Inventors: Antti Salopuro, Varkaus (FI); Pekka Lehtikoski, Alpharetta, GA (US)

(73) Assignee: Metso Automation Oy, Helsinki (FI)

( * ) Notice: Subject to any disclaimer, the term of this patent is extended or adjusted under 35 U.S.C. 154(b) by 2664 days.

(21) Appl. No.: 11/118,052

(22) Filed: Apr. 29, 2005

(65) Prior Publication Data

US 2005/0249411 A1    Nov. 10, 2005

Related U.S. Application Data (60) Provisional application No. 60/567,941, filed on May 4, 2004.

(51) Int. Cl.
| | |
|---|---|
| *G01N 1/22* | (2006.01) |
| *G01N 15/06* | (2006.01) |
| *G01N 21/49* | (2006.01) |
| *G01N 21/85* | (2006.01) |
| *G01N 15/02* | (2006.01) |
| *G08B 21/00* | (2006.01) |
| *G06K 9/00* | (2006.01) |
| *G06K 9/46* | (2006.01) |
| *G06K 9/66* | (2006.01) |

(52) U.S. Cl.
USPC .......... 382/141; 382/168; 382/192; 356/335; 356/338; 250/574; 340/627; 73/864

(58) Field of Classification Search
USPC ............ 73/864; 250/574; 340/507, 627–628
See application file for complete search history.

(56) References Cited

U.S. PATENT DOCUMENTS

| 4,288,162 | A | | 9/1981 | Sakamoto et al. |
|---|---|---|---|---|
| 4,986,659 | A | * | 1/1991 | Bachalo ................ 356/336 |
| 5,126,581 | A | * | 6/1992 | Furuya et al. ............ 250/574 |
| 5,247,461 | A | * | 9/1993 | Berg et al. ................ 702/26 |
| 5,309,215 | A | * | 5/1994 | Schumann ............. 356/335 |
| 5,317,650 | A | * | 5/1994 | Harrington ............. 382/199 |
| 5,721,433 | A | * | 2/1998 | Kosaka ................... 250/573 |
| 5,825,477 | A | | 10/1998 | Furuie |
| 6,317,511 | B1 | * | 11/2001 | Horiuchi ................. 382/133 |
| 2002/0036776 | A1 | * | 3/2002 | Shimaoka ............. 356/336 |
| 2002/0071596 | A1 | * | 6/2002 | Estevez ................. 382/107 |
| 2005/0046841 | A1 | | 3/2005 | Rabinski et al. |
| 2007/0165225 | A1 | * | 7/2007 | Trainer ................... 356/335 |

FOREIGN PATENT DOCUMENTS

| JP | 9089748 | 4/1997 |
|---|---|---|
| JP | 2001337028 | 12/2001 |

OTHER PUBLICATIONS

Search Report for International Application No. PCT/FI2005/050142 mailed Jul. 25, 2005.

* cited by examiner

*Primary Examiner* — Randolph I Chu
*Assistant Examiner* — Nathan Bloom
(74) *Attorney, Agent, or Firm* — Alston & Bird LLP (57) ABSTRACT

The solution provides a frequency distribution of a dimension of objects projected onto an image, the distribution being generated by measuring the dimension of the objects in a space in which the position of each object is at least partly free, the dimension of each object in the image depending on the position of the object. The frequency distribution of the projected objects is weighted by a weighting operation compensating for the impact of the projection in order to generate a real frequency distribution of the objects.

29 Claims, 2 Drawing Sheets

GENERATION OF FREQUENCY DISTRIBUTION FOR OBJECTS

CROSS-REFERENCE TO RELATED APPLICATIONS

This application claims the benefit of U.S. Provisional Application No. 60/567,941 filed May 5, 2004, which is incorporated herein in its entirety.

BACKGROUND OF THE INVENTION

1) Field of the Invention

The invention relates to generating a frequency distribution for dimensions of objects to be imaged, such as fibers used in pulp and paper processes.

2) Description of Related Art

Paper industry, for example, uses pulp processes in which the average length of fibers and the distribution of their length are often among the most essential parameters. Length distribution is usually expressed as proportional frequencies (weighted by length) of different length categories, and thus the values of the length categories can be interpreted as percentage shares of the entire pulp mass.

One method of measuring these parameters is to produce an image of a pulp suspension of low consistency, with the fibers in the suspension dispersed into water acting as a medium, and to aim at determining, by means of an automated image processing equipment, a representative amount of sample fibers from the pulp to establish the nature of the pulp. A similar method can be used to measure other objects than pulp as well.

However, this measurement involves problems. When objects to be imaged are in a space in which the position of each object is at least partly free and when the dimension of each object in the image depends on its position, the projected dimension of the object can be measured from the image. The projection distorts the frequency distribution of the dimensions of the objects and thus measurements carried out this way do not correspond to reality. Moreover, if the space that is being imaged is smaller than the space in which the objects are allowed to move, the margin of the image forms an area in which only the part of the object that is within the margin can be imaged, and thus it is not possible to determine the real dimension of the object. Further, in the middle of the image there may be discontinuities caused by impurities or cracks in the measurement optics, which will affect the visibility of the dimensions and their measurement.

BRIEF SUMMARY OF THE INVENTION

It is an object of the invention to provide an improved method, computer program, and a measuring device.

This is achieved by a method for determining a frequency distribution for dimensions of objects, in which method there is available an image from which the frequency distribution of imaged objects is determined; the method comprising modifying the frequency distribution of the dimensions of the objects measured from the image by a weighting operation associated with a probability of the real dimensions of the objects being imaged in the image.

Further, this is achieved by a method for determining a frequency distribution for dimensions of objects, in which method there is available a frequency distribution of the dimensions of objects projected onto an image; the frequency distribution is generated by measuring a dimension of the objects in a space in which the position of each object is at least partly free; and the dimension of each object in the image depends on the position of the object, the method comprising modifying the frequency distribution of the dimensions of the projected objects by a weighting operation cancelling the impact of the projection in order to generate a real frequency distribution of the objects.

Further, this is achieved by a method for determining a frequency distribution for dimensions of objects, in which method there is available an image from which the frequency distribution of the dimensions of imaged objects is determined; some of the objects are entirely imaged in the image, and some of the objects are partly imaged in the image, the method comprising modifying the frequency distribution of the dimensions of objects measured from the image by a correction operation associated with the dimensions of the image, the dimensions of the objects in the image, and the location of the objects in the image.

The invention also relates to a computer program for executing a computer process which, when being executed, determines a frequency distribution for a dimension of objects, in which the frequency distribution of the dimension of the imaged objects determined from an image is supplied to the computer program, the computer process comprising modifying the frequency distribution of the dimensions of the objects measured from the image by a weighting operation associated with a probability of the real dimensions of the objects being imaged to the image.

The invention further relates to a computer program for executing a computer process which, when being executed, determines a frequency distribution for a dimension of objects, in which the frequency distribution of the dimensions of the objects projected onto the image is supplied to the computer program, the frequency distribution being generated by measuring the dimension of the objects in a space in which the position of each object is at least partly free, the dimension of each object in the image depending on the position of the object, the computer process comprising modifying the frequency distribution of the dimensions of the projected objects by a weighting operation cancelling the impact of the projection in order to generate a real frequency distribution of the objects.

The invention further relates to a computer program for executing a computer process which, when being executed, determines a frequency distribution for a dimension of objects, in which the frequency distribution of the dimensions of objects determined from an image are supplied to the computer program; some of which objects are entirely imaged in the image and some of the objects are partly imaged in the image, the computer process comprising modifying the frequency distribution of the dimensions of the objects measured from the image by a correction operation associated with the dimensions of the image, the dimensions of the objects in the image, and the location of the objects in the image.

The invention further relates to a measuring device for determining a frequency distribution for dimensions of objects, the measuring device comprising a signal processing unit configured to receive the frequency distribution of the dimensions of the imaged objects; and the signal processing unit is configured to modify the frequency distribution of the dimensions of the objects measured from the image by a weighting operation associated with a probability of the real dimensions of the objects being imaged in the image.

The invention still further relates to a measuring device for determining a frequency distribution for a dimension of imaged objects, the measuring device comprising a signal processing unit configured to receive the frequency distribution of the dimension of the objects projected onto the image, the frequency distribution being generated by measuring the dimension of the objects in a space in which the position of each object is at least partly free, the dimension of each object in the image depending on the position of the object, and the signal processing unit is configured to modify the frequency distribution of the dimension of the projected objects by a weighting operation compensating for the impact of the projection in order to generate a real frequency distribution of the objects.

The invention still further relates to a measuring device for determining a frequency distribution for a dimension of imaged objects, the measuring device comprising a signal processing unit configured to receive the frequency distribution of objects determined from the image, in which image some of the objects are entirely imaged and some of the objects are partly imaged, and the signal processing unit is configured to modify the frequency distribution of the dimensions of the objects measured from the image by a correction operation associated with the dimensions of the image, the dimensions of the objects in the image, and the location of the objects in the image.

Preferred embodiments of the invention are disclosed in the dependent claims.

The method and system of the invention provide several advantages. The impact of the position of the objects can be eliminated from the frequency distribution calculated from a dimension of objects measured from an image, and thus it is possible to generate an unbiased frequency distribution. Similarly it is possible to eliminate from the frequency distribution the impact of an image margin or some other similar element of the measuring arrangement that splits the images of individual objects or otherwise changes their dimensions projecting onto the image plane.

BRIEF DESCRIPTION OF THE DRAWINGS

In the following the invention will be described in greater detail with reference to the preferred embodiments and the accompanying drawings, in which.

DETAILED DESCRIPTION OF THE INVENTION

Figure 1:
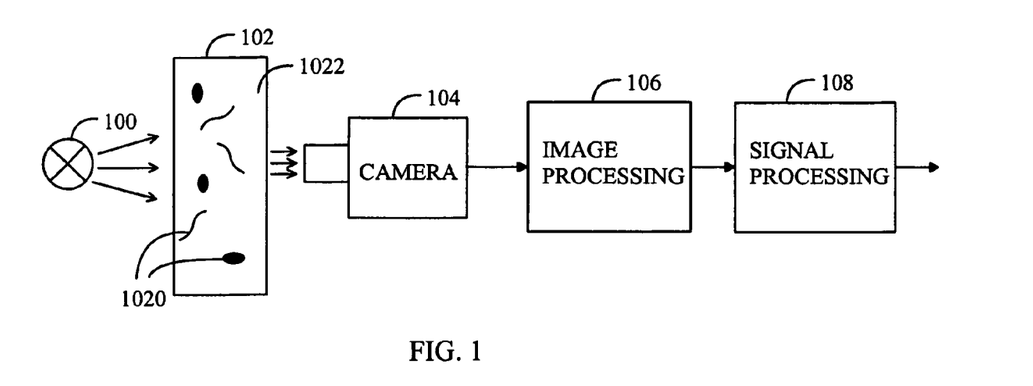
FIG. 1 illustrates a measuring arrangement.

The frequency distribution of the dimensions objects can be measured as shown in FIG. 1, for example. An optical radiation source 100 is used for focusing optical radiation to a measuring cell 102 having objects consisting of a low-consistency suspension containing wood fibers, for example (the consistency may vary between 0.001% and 0.003%, although it is not restricted thereto). In addition to wood fibers, the objects 1020 may consist of fine particulate matter 1020 present in a medium 1022. In a general case, most diversified particles of solid substances, liquid substances, or gaseous substances, instead of a fiber suspension, may be dispersed into a liquid medium. Moreover, in a general case, particles of a liquid substance or a solid substance may be dispersed into a gaseous medium. Instead of particles, large pieces can be measured as well, and the measurement may be carried out without a medium.

The optical radiation source 100 may emit an ultraviolet radiation, visible light, or infrared radiation. A camera sensitive to optical radiation and comprising a detecting pixel matrix may be used as a detector 104. The pixel matrix may be a semiconductor component, such as a CCD (Charge-Coupled Device) cell. As the optical radiation focused to the measurement cell 102 exits from the cell 102, a desired image of the combination of the particles and the medium inside the measurement cell 102 can be formed to the detector 104 by means of an image-forming optical component, such as a lens. The optical radiation source 100 and the detector 104 may be on opposite sides of the measurement cell 102, whereby the cell 102 is transilluminated.

Each pixel in the detector 104 converts the intensity of optical radiation it encounters to an electronic signal. The generated electrical signals are converted to a digital image data signal, which is then supplied to an automated image-processing unit 106.

The image-processing unit 106 may measure the dimensions of the objects and generate a frequency distribution for the dimensions of the imaged objects. The generated frequency distribution data may be supplied to a separate signal-processing unit 108, or to the image-processing unit 106, which may include the signal-processing unit 108. The signal-processing unit 108 modifies the frequency distribution of the dimensions of the imaged objects in order to generate the real frequency distribution of the dimensions of the objects. The frequency distribution for the dimensions of the imaged objects may be generated and this distribution modified separately and independently from each other, but equally well they may be part of the same signal processing process.

Figure 2:
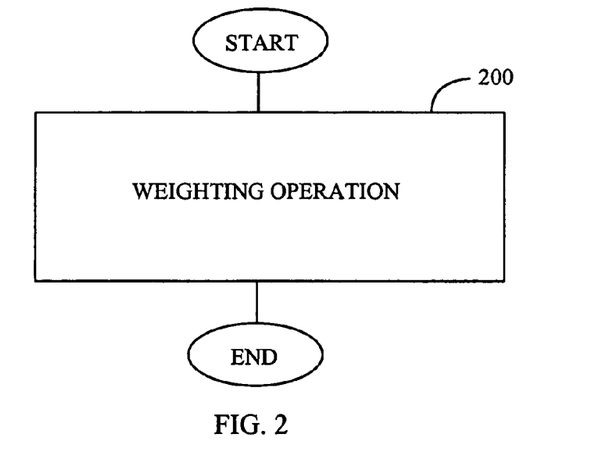
FIG. 2 is a flow diagram of the method.

Examine next the disclosed method with reference to FIG. 2. The method steps may be executed in the signal-processing unit 108. In the method there is available a frequency distribution of a dimension of objects projected onto the image, generated by measuring the dimension of the objects. The measurement is carried out in a space the size of which allows each object to assume a position that is at least partly free. In addition, the dimension of each object in the image depends on its position in the measurement space, which may be the space projected onto the image to be generated, this space being restricted in the depth direction by the walls of the measurement cell, for example. The dimension of each object in the image depends on the position of the object. In method step 200 the frequency distribution of the dimensions of the objects measured from the image are modified by a weighting operation associated with the probability of the real dimensions of the objects being imaged in the image.

Next, examine the projection involved in the imaging in greater detail. The objects to be imaged, such as wood fibers in a fiber suspension, assume different random positions in the measuring cell if the dimensions of the cell are greater than those of the object. The objects are also in random locations. In that case a dimension determining an object imaged in the image plane is probably smaller than in reality and therefore a projected dimension is always at the most equal to the real dimension of an object. Since the position of an individual object is impossible to know, the real dimension of the object cannot be determined with precision. However, when a large set of objects is imaged in one sample and the probability, or statistical dependency, associated with the position of the objects in the space to be measured is known, the frequency distribution of the measured projection lengths can be converted to the real frequency distribution of the objects. The frequency distribution converted from the frequency distribution of the dimensions thus projected corresponds to a measurement made from an image in which the dimension of each object is imaged in full length, i.e. in which the projection length, for example, is the same as the real length of an object.

According to a basic principle, the frequency distribution of the projected dimensions of objects can be modified by a weighting operation based on the probability of the positions of the objects.

Examine then a large set of objects that is being imaged. A sample shows that an individual object may assume at least partly in any position and any location in the image area. Also the impact of the position or location of an individual object, a sample state, or some other interfering factor on the dimension of the object's projection is known, and the average combined effect of these can be determined. Since the average combined effect is known, a transfer function $f(x,y)$ can be defined to illustrate the interdependency between the real dimensions x of the objects and the dimensions y of their projections.

Let the number of objects in a large sample be N and let the projection lengths of imaged objects be grouped into categories according to a dimension to be measured, and let the number of categories be k and a dimension measure corresponding to the last category be at least equal to the real dimension (such as length) of the largest object in the entire set of objects. The dimension measure corresponding to the last category may also be the dimension measure of the smallest object (an inverse of its length, for example). Let $N_x$ be the number of objects really belonging to category x, and $n_y$ the number of projected objects in category y, and let symbol $n_{x,y}$ denote the number of objects that are real objects of category x, but projected objects in category y. Thus $n_y$ may be expressed as $$n_y = \sum_{x=y}^{k} n_{x,y} \tag{1}$$

and $N_x$ as $$N_x = \sum_{y=1}^{x} n_{x,y} \tag{2}$$

In order to be able to generate the real distribution of the dimensions of the objects, it must be possible to define the values of $N_x$ for all x's. Thus, quantities $n_y$ are known, whereas quantities $nx_y$ are generally not known. However, if it is possible to define transfer function $f(x,y)$ for example such that $$f(x, y) = \frac{N_x}{n_{x,y}}, \tag{3}$$

then quantities $N_x$ can be calculated.

If the imaging arrangement only allows a decrease in projection dimensions (or, correspondingly, only an increase) in imaging, and if N is large enough, it can be assumed that there is a category $x_{max}$ containing only projected objects whose real dimension also belongs to the same a category $x_{max}$. This category corresponds to the greatest (or, correspondingly, smallest) dimension of this type and has a projection length of at least one object classified therein. Let thus $n_{xmax,xmax}$ be the number of objects whose real dimension belongs to dimension category $x_{max}$ and which are also projected to category $x_{max}$. With the average impact the position or location of objects, a sample state, or some other interfering factor has on an object's projection length known, transfer function $f(x,y)$ may be defined and used for calculating $n_{xmax,y}$ $$f(x_{max}, y) \cdot n_{xmax,xmax} = n_{xmax,y}, \tag{4}$$

for all y's.

Let then $x_{max-1}$ be the category closest in size preceding (or following) category $x_{max}$, whereby the following is valid:

$$n_{xmax-1} = n_{xmax-1,xmax-1} + n_{xmax,xmax-1}. \tag{5}$$

Since the transfer function values at points (xmax, y) are known, quantity $n_{xmax,xmax-1}$ is known. Similarly, $n_{xmax-1}$ is also known and thus the quantity can be calculated from the above equation. Further, it is possible to calculate $$f(x_{max-1}, y) \cdot n_{xmax-1,xmax-1} = n_{xmax-1,y} \tag{6}$$

for all y's. By continuing this, eventually all quantities $n_{x,y}$ can be calculated from which follows that all quantities $N_x$ can be calculated as well.

A transfer function correcting an average projection distortion caused by the position of the objects can be normalized by means of a function representing the probability of the objects' position by dividing a corresponding noncontinuous probability function by the value of its highest category, the category thus obtaining always the value one ($f(x,x)=1$), or some other pre-determined value, and the lower categories can then be weighted accordingly. In other words, when it is possible to define the probability function analytically (or by means of simulation or test measurements) in such a way that it can be expressed as a continuous function, the probability of the category comprising the largest objects can be determined as an integral of the probability function from the lower limit of the dimension of the largest category to its upper limit. Correspondingly, it is possible to make the probability function discrete for lower categories and then a transfer function can be deduced, as will be disclosed below.

Figure 3:
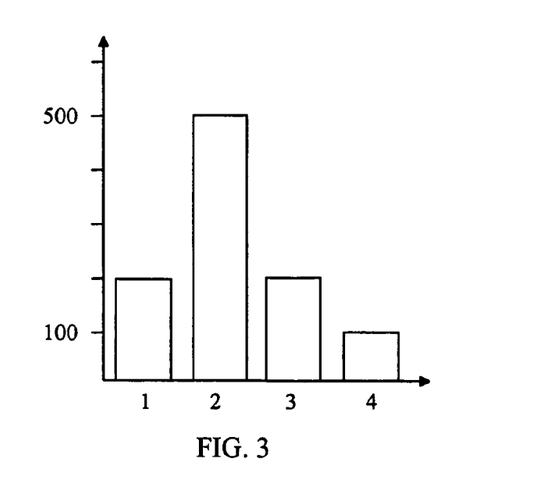
FIG. 3 illustrates a frequency distribution measured from an image.

Examine then an example in which $n_y = \{200, 500, 200, 100\}$, $y \in \{1, 2, 3, 4\}$ represent the frequency distribution of the object lengths measured from a sample of 1000 objects. FIG. 3 shows the frequency distribution measured from the image. The horizontal axis depicts the length category and the vertical axis the number of objects in each category.

The imaging arrangements are such that all the objects are imaged in the image plane in a length corresponding to their real dimension at the most. Projection length transfer function $f(x,y)$ corresponding to the measurement situation can be determined as follows:

$$f(x, y) = \begin{cases} 1, & \text{when } y = x \\ \frac{1}{10}, & \text{when } y < x \end{cases} \tag{7}$$

In the initial phase the following data is available on the measured dimensions of the objects:

| | 1 | 2 | 3 | 4 | Σ = $n_x$ |
|---|---|---|---|---|---|
| 1 | $n_{1,1}$ | $n_{2,1}$ | $n_{3,1}$ | $n_{4,1}$ = 10 | 200 |
| 2 | $n_{1,2}$ = 0 | $n_{2,2}$ | $n_{3,2}$ | $n_{4,2}$ = 10 | 500 |
| 3 | $n_{1,3}$ = 0 | $n_{2,3}$ = 0 | $n_{3,3}$ = 200 − 10 = 190 | $n_{4,3}$ = 10 | 200 |
| 4 | $n_{1,4}$ = 0 | $n_{2,4}$ = 0 | $n_{3,4}$ = 0 | $n_{4,4}$ = 100 | 100 |
| Σ = $N_x$ | | | | 130 | |

In the first step of the algorithm, the number of objects belonging to category 4 and the corresponding numbers of objects to be removed from shorter categories are calculated, and thus $n_{3,3}$ can be solved as follows:

$$N_4 = \sum_{y=1}^{4} f(4, y) \cdot n_{4,4}$$

$$= (1/10) \cdot 100 + (1/10) \cdot 100 + (1/10) \cdot 100 + 1 \cdot 100$$

$$= 130,$$

|   | 1 | 2 | 3 | 4 | $\Sigma = n_x$ |
|---|---|---|---|---|---|
| 1 | $n_{1,1}$ | $n_{2,1}$ | $n_{3,1}$ | $n_{4,1} = 10$ | 200 |
| 2 | $n_{1,2} = 0$ | $n_{2,2}$ | $n_{3,2}$ | $n_{4,2} = 10$ | 500 |
| 3 | $n_{1,3} = 0$ | $n_{2,3} = 0$ | $n_{3,3} = 200 - 10 = 190$ | $n_{4,3} = 10$ | 200 |
| 4 | $n_{1,4} = 0$ | $n_{2,4} = 0$ | $n_{3,4} = 0$ | $n_{4,4} = 100$ | 100 |
| $\Sigma = N_x$ |   |   |   | 130 |   |

In step two, in which the category of the second largest dimensions is modified, the following result is obtained:

$$N_3 = \sum_{y=1}^{3} f(3, y) \cdot n_{3,3}$$

$$= n_{3,1} + n_{3,2} + n_{3,3}$$

$$= (1/10) \cdot 190 + (1/10) \cdot 190 + 1 \cdot 190$$

$$= 228$$

and thus $n_{2,2}$ can be solved:

|   | 1 | 2 | 3 | 4 | $\Sigma = n_x$ |
|---|---|---|---|---|---|
| 1 | $n_{1,1}$ | $n_{2,1}$ | $n_{3,1} = 19$ | $n_{4,1} = 10$ | 200 |
| 2 | $n_{1,2} = 0$ | $n_{2,2} = 500 - 10 - 19 = 471$ | $n_{3,2} = 19$ | $n_{4,2} = 10$ | 500 |
| 3 | $n_{1,3} = 0$ | $n_{2,3} = 0$ | $n_{3,3} = 190$ | $n_{4,3} = 10$ | 200 |
| 4 | $n_{1,4} = 0$ | $n_{2,4} = 0$ | $n_{3,4} = 0$ | $n_{4,4} = 100$ | 100 |
| $\Sigma = N_x$ |   |   | 228 | 130 |   |

In the third step, in which the category of the third largest dimensions is modified, the following result is obtained:

$$N_2 = \sum_{y=1}^{2} f(2, y) \cdot n_{2,2}$$

$$= n_{2,1} + n_{2,2}$$

$$= (1/10) \cdot 471 + 1 \cdot 471$$

$$= 518.1,$$

and thus $n_{1,1}$ and, thereby, the real number $N_1$ of objects in category 1 can be solved.

|   | 1 | 2 | 3 | 4 | $\Sigma = n_x$ |
|---|---|---|---|---|---|
| 1 | $n_{1,1} = 200 - 10 - 19 - 47.1 = 123.9$ | $n_{2,1} = 47.1$ | $n_{3,1} = 19$ | $n_{4,1} = 10$ | 200 |
| 2 | $n_{1,2} = 0$ | $n_{2,2} = 471$ | $n_{3,2} = 19$ | $n_{4,2} = 10$ | 500 |
| 3 | $n_{1,3} = 0$ | $n_{2,3} = 0$ | $n_{3,3} = 190$ | $n_{4,3} = 10$ | 200 |
| 4 | $n_{1,4} = 0$ | $n_{2,4} = 0$ | $n_{3,4} = 0$ | $n_{4,4} = 100$ | 100 |
| $\Sigma = N_x$ | 123.9 | 518.1 | 228 | 130 |   |

Figure 4:
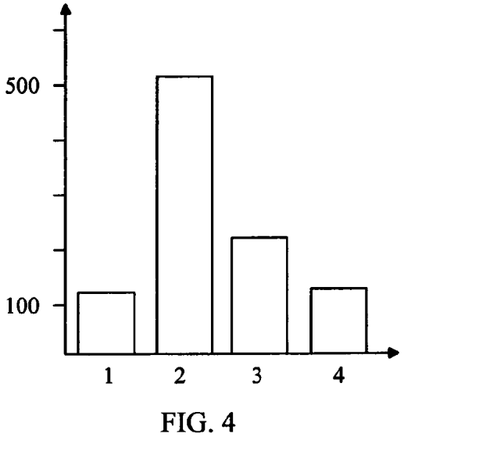
FIG. 4 illustrates a frequency distribution from which the impact of projection has been rectified.

FIG. 4 shows a modified distribution. The horizontal axis depicts the length category and the vertical axis the number of objects in each category.

In some cases transfer function f(x,y) can be analytically deduced from a setting associated with the measurement, for example for entirely freely positioned straight fibers in a large three-dimensional space. More often, however, the probability function is either obtained as a result of simulation or defined on the basis of measurements of objects known in advance.

Examine then briefly the interdependency between a transfer function and probability functions by means of the example below. Assume that it is possible to analytically define frequency function $$p(x, y) = \frac{\frac{y}{x}}{\sqrt{1 - \left(\frac{y}{x}\right)^2}} \tag{8}$$

which represents the frequency distribution of objects of dimension x in relation to project dimension y<x. The probability $P(y1 < y \leq y2)$ that an object whose real dimension is x sets to a position or place where its projection length is within ]y1,y2] can then be calculated using cumulative distribution function $$P(y1 < y \leq y2) = \int_{y1}^{y2} \frac{\frac{y}{x}}{\sqrt{1 - \left(\frac{y}{x}\right)^2}} \, dy \tag{9}$$

or, more generally, with $$P(y1 < y \leq y2) = \int_{y1}^{y2} p(x, y) \, dy,$$

i.e. the frequency function integral within a corresponding range.

Let the object categories be defined such that the width of one category is x/N, and let the corresponding categories be labeled with symbols (Y1, Y2, Y3, . . . , YN). By means of a cumulative distribution function it is now possible to define a corresponding transfer function f(YN, Yn)

$$f(YN, Yn) = \frac{P(y \in Yn)}{P(y \in YN)}. \tag{10}$$

Similarly, it is possible to determine a general interdependency between the probability function and the transfer function, but instead of analytic deduction, it may be necessary to resort to approximations, simulation and/or practical testing.

The frequency distribution of the dimensions of objects measured from an image can be modified by a weighting operation associated with the probability of the objects' real dimensions being imaged in the image also in situations where an object is on the margin of the image with only part of the dimension to be measured visible. The location of an object has an impact on the length of the projection for example when a part of an object that happens to be on the margin of the image is left out of the image. Since it is not possible to measure a part of an individual object that is outside the image area, the real length of that object cannot be determined with precision. However, the probability associated with the length of the part of the object within the image is almost evenly distributed along the entire length on the margins of rectangular images when the dimensions of the object are small in relation to the dimensions of the image. For images of some other shape, such as round, the distribution of probability is not necessarily uniform but can be deduced or determined by means of simulation or testing. In practical applications, however, deviation from a uniform distribution is so small that an assumption of uniform distribution can be applied. In addition, since one sample contains a large set of objects to be imaged and the random function of length determined by object location is known, information on the distribution of measured lengths can be modified such that on the average the distribution is the same as it would be if each fiber had been measured perpendicularly against its vertical axis, without the margins of the image being exceeded. However, the corner areas of an image increase the relative proportion of the smallest projected lengths in comparison with the larger projection dimension categories, but the impact of this often so small that it can be ignored.

The ratio of objects entirely in the image to those only partly there can be expressed as a function of object length (or width) and image dimensions; however, this is applied to each case separately, and depends on the measuring arrangements. With this ratio it is possible to define a probability function modifying dimensions to allow the projection dimensions of objects imaged in the margins of an image and partly outside thereof to be determined. After the probable projection dimensions of objects imaged in the margins have been determined, it is possible to generate a frequency distribution of all dimensions of (partly or entirely) imaged objects, and the distribution can be modified according to the method disclosed above. The probability function associated with objects imaged in the margins can be deduced analytically or determined by means of simulation or testing.

Let an image have a size of 5 cm×5 cm=25 cm² and all objects to be measured a length of l=2 cm, for example. In this case an object will fit into the image with certainty if the distance of its midpoint from the margin is greater than 1 cm, i.e. it will be in the mid-area 3 cm×3 cm=9 cm² of the image. If the midpoint of the object is inside the image and its distance from the margin of the image is less than 1 cm, the probability of the entire object of fitting into the image is about 28%, i.e. at a probability of about 72% it will be on the margin. Further, if the midpoint of the object is outside the image at a distance of 1 cm at the most from the margin, there is a probability of 48% that a part of the object will extend over the image margin. The surface area of the margin within the borders of the image is 25 cm²−9 cm²=16 cm² and the corresponding surface area of the margin on the outside is about 21.56 cm², but only 48% of it, i.e. 10.34 cm², needs to be taken into account. The entire surface area to be taken into account is thus 25 cm²+10.34 cm²=35.34 cm². It is now possible to calculate that if an object is at least partly in the image area, it will fit entirely into the image, i.e. with a probability P the projection length p is the same as the object length l:

$$P(p=l)=100\%\cdot[9\cdot1.0+16\cdot0.28+21.56\cdot0.0]/35.34\approx38.1\%$$

Correspondingly, with a probability P the object is only partly in the image:

$$P(p<l)=100\%\cdot(1.0-0.381)\approx61.9\%$$

Let the image have the above dimensions, the measure applied between categories be $\Delta l=0.1$ cm, and let category 2.00-2.1 cm contain 38 objects grouped therein as a result of measurement, and assume that the measured frequency of this category does not contain any objects belonging to a category consisting of objects whose real lengths are longer. It is thus known that the image contains n partial objects $$n=0.619\cdot38/0.381\approx61.73$$

Assuming that the objects partly shown in the image are uniformly distributed as regards their lengths that are shorter than the real length, the corresponding transfer function is $$f(l, p) = \begin{cases} 1, & \text{when } p = 1 \\ 0.0812, & \text{when } p < 1 \end{cases}, \quad (11)$$

where the value 0.0812 of function f(l, p) is arrived at by multiplying the ratio of objects partly in the image to those entirely in it by the ratio of the category range to the length of the objects to be measured $(P(p<l)/P(p=l))\cdot(\Delta l/l)=(0.619/0.381)\cdot(0.1 \text{ cm}/2 \text{ cm})\approx0.0812$.

The bending or breaking of an object has a significant impact on its projection length. Compared with a situation where the objects are entirely straight, it is much more complicated to define the probability and the transfer function by means of analytical deduction. However, simulation and measurement of known samples may be used for determining an approximation that is sufficiently precise for practical purposes. The curliness C of an object can be defined by means of the following formula:

$$C=100\cdot(1-\delta/l), \quad (12)$$

where δ is the shortest distance between the ends of an object and l is the length of the midline of the object. The impact of the projection can be cancelled from both of these dimensions by means of the disclosed method. In each dimension category can be determined as a function of the object's curliness. However, an analytic function is complicated to deduce, and in view of the object of application it is therefore often appropriate to determine the function only by means of simulation or by measuring known objects.

Figure 5:
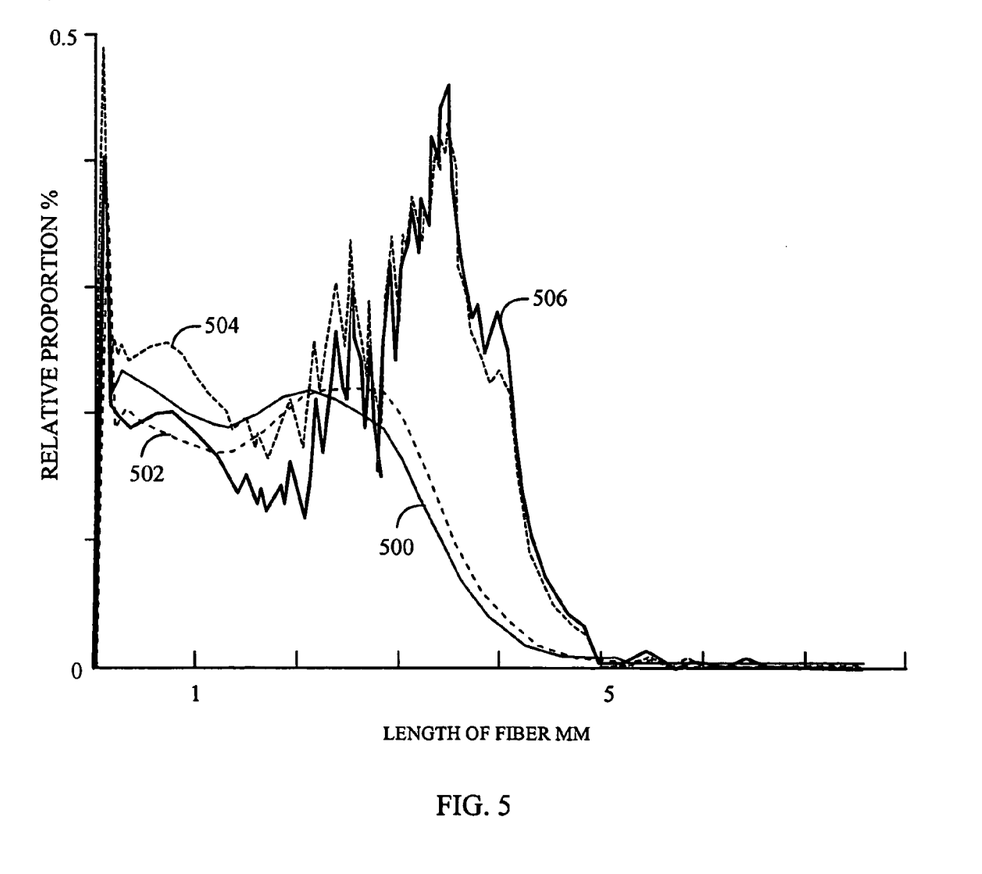
FIG. 5 illustrates frequency distributions associated with the length measurement of wood fibers.

FIG. 5 shows a frequency distribution measured from an image, and modified frequency distributions. The curves depict the length distribution of wood fibers, the horizontal axis representing fiber length and the vertical axis the relative proportion. Curve 500 depicts an unmodified frequency distribution measured from the image and curve 502, in turn, a frequency distribution in which the impact of the image margins on the distribution has been cancelled. Curve 504 depicts a frequency distribution in which the impact of the projections of the fibers to the frequency distribution has been cancelled. Further, curve 506 depicts the real frequency distribution of the wood fibers, both the impact of the image margin and the projection having been cancelled from the distribution by the method described above.

Other factors that may have an impact on object dimensions include litter, cracks or other similar flaws in the measurement optics, a broken light detector, a set of detectors, a row of pixels, or the like, in a camera, the distance of the object in depth direction from the imaging plane, distortion in the image projection due to the location of the object (e.g. what is known as fish-eye optics), physical compression or swelling of objects, or changes in the speed of movement of the objects. Any changes to the frequency distribution caused by these can be eliminated by modifying the frequency distribution of the object dimensions measured from an image by a weighting operation associated with the probability of the real object dimensions being imaged in the image.

Both the image-processing unit 106 and the signal-processing unit 108 can be implemented as a processor and software, and the disclosed method can be implemented as a computer program. Likewise, the signal processing unit 108 as well as the image-processing unit 106 can alternatively be implemented in the form of a hardware configuration by means of separate logic components or one or more Application-Specific Integrated Circuits (ASIC). Also a hybrid of these different implementations is possible.

The method can be implemented as a computer program product to be installed to a signal processing unit and encoding a computer process for determining a frequency distribution for object dimensions. This computer process conforms to the disclosed method. The computer program product can be stored to a computer program distribution medium. The distribution medium can be read by means of a computer executing the program (the signal processing unit). The delivery means may be any known means for delivering a computer program from a manufacturer/supplier to an end user. The delivery means may be for example a medium readable by the signal processing unit, a program storage medium, a memory readable by the signal processing unit, a telecommunications signal addressed to the end user (or the signal processing unit) by the manufacturer/supplier, or a compressed software package.

Although the invention is disclosed above with reference to an example according to the accompanying drawings, it is obvious that the invention is not restricted thereto but can be modified in many ways within the scope of the accompanying drawings.

That which is claimed:

1. A method for determining a frequency distribution for dimensions of objects, in which method there is available an image from which the frequency distribution of imaged objects is determined; the method comprising
    defining a measured dimension of an object in the image being a real dimension; and
    modifying, via a processor, the frequency distribution of the dimensions of the objects measured from the image by a weighting operation associated with a probability of the real dimensions of the objects being imaged in the image.

2. A method according to claim 1, the method further comprising determining the curliness of the objects, the object dimensions measured from the image and needed for measuring the curliness being modified by a weighting operation associated with a probability of the real dimensions of the objects being imaged in the image.

3. A method for determining a frequency distribution for dimensions of objects, in which method there is available a frequency distribution of the dimensions of objects projected onto an image;
    the frequency distribution is generated by measuring a dimension of the objects in a space in which the position of each object is at least partly free; and
    the dimension of each object in the image depends on the position of the object and is a real dimension, the method comprising
    modifying, via a processor, the frequency distribution of the dimensions of the projected objects by a weighting operation cancelling the impact of the projection in order to generate a real frequency distribution of the objects.

4. A method according to claim 3, the method comprising weighting the frequency distribution of the dimension of the projected objects by a weighting operation associated with a probability relating to the positions of the objects.

5. A method according to claim 3, the method comprising weighting the frequency distribution of the dimension of the projected objects by an algorithm serving as the weighting operation, the frequency distribution including categories in which each category in the frequency distribution of the dimension of the projected objects is weighted by an inter-category probability associated with the position of the objects.

6. A method according to claim 3, which method comprises, when the frequency distribution of the dimension of the projected objects includes categories,
    weighting each category by adding portions thereto, according to a function compensating for the impact of the projection, from other categories representing a smaller dimension, the categories being processed in order from a category representing the largest dimension to a category representing the smallest dimension.

7. A method according to claim 3, which method comprises, when the frequency distribution of the dimension of the projected objects includes categories,
    weighting each category by adding thereto, according to a function compensating for the impact of the projection, numbers of objects from other categories representing a smaller dimension, the categories being processed in order from a category representing the largest dimension to a category representing the smallest dimension.

8. A method for determining a frequency distribution for dimensions of objects, in which method there is available an image from which the frequency distribution of the dimensions of imaged objects is determined;
    some of the objects are entirely imaged in the image, and some of the objects are partly imaged in the image, the method comprising
    defining a measured dimension of an object in the image being a real dimension; and
    modifying, via a processor, the frequency distribution of the dimensions of objects measured from the image by a correction operation associated with the dimensions of the image, the dimensions of the objects in the image, and the location of the objects in the image.

9. A computer program product comprising at least one computer-readable storage medium having computer-readable program code portions stored therein, the computer-readable program code portions for executing a computer process which, when being executed, determines a frequency distribution for a dimension of objects, in which the frequency distribution of the dimension of the imaged objects determined from an image is supplied to the computer program product, the computer process comprising
    defining a measured dimension of an object in the image being a real dimension; and modifying the frequency distribution of the dimensions of the objects measured from the image by a weighting operation associated with a probability of the real dimensions of the objects being imaged to the image.

10. A computer program product according to claim 9, which computer program product further comprises code portions for determining the curliness of objects, the dimensions measured from an image and needed for measuring the curliness being modified by a weighting operation associated with a probability of the real dimensions of the objects being imaged in the image.

11. A computer program product comprising at least one computer-readable storage medium having computer-readable program code portions stored therein, the computer-readable program code portions for executing a computer process which, when being executed, determines a frequency distribution for a dimension of objects, in which the frequency distribution of the dimensions of the objects projected onto the image is supplied to the computer program, the frequency distribution being generated by measuring the dimension of the objects in a space in which the position of each object is at least partly free, the dimension of each object in the image depending on the position of the object, the computer process comprising defining a measured dimension of an object in the image being a real dimension; and modifying the frequency distribution of the dimensions of the projected objects by a weighting operation cancelling the impact of the projection in order to generate a real frequency distribution of the objects.

12. A computer program product according to claim 11, the computer program product comprising code portions for weighting the frequency distribution of the dimension of the projected objects by a weighting operation associated with a probability relating to the positions of the objects.

13. A computer program product according to claim 11, the computer program comprising weighting the frequency distribution of the dimension of the projected objects by an algorithm serving as the weighting operation, the frequency distribution including categories in which each category in the frequency distribution of the dimension of the projected objects being weighted by an inter-category probability associated with the position of the objects.

14. A computer program product according to claim 11, which computer program product comprises code portions for, when the frequency distribution of the dimension of the projected objects includes categories, weighting each category by adding portions thereto, according to a function compensating for the impact of the projection, from other categories representing a smaller dimension, the categories being processed in order from a category representing the largest dimension to a category representing the smallest dimension.

15. A computer program product according to claim 11, which computer program product comprises code portions for, when the frequency distribution of the dimension of the projected objects includes categories, weighting each category by adding thereto, according to a function compensating for the impact of the projection, numbers of objects from other categories representing a smaller dimension, the categories being processed in order from a category representing the largest dimension to a category representing the smallest dimension.

16. A computer program product according to claim 11, the computer program product further comprising code portions for determining a dimension for objects imaged in the margin of the image and therefore partly outside the image by means of a probability function modifying the measured dimensions.

17. A computer program product comprising at least one computer-readable storage medium having computer-readable program code portions stored therein, the computer-readable program code portions for executing a computer process which, when being executed, determines a frequency distribution for a dimension of objects, in which the frequency distribution of the dimensions of objects determined from an image are supplied to the computer program; some of which objects are entirely imaged in the image and some of the objects are partly imaged in the image, the computer process comprising defining a measured dimension of an object in the image being a real dimension; and modifying the frequency distribution of the dimensions of the objects measured from the image by a correction operation associated with the dimensions of the image, the dimensions of the objects in the image, and the location of the objects in the image.

18. A measuring device for determining a frequency distribution for dimensions of objects, the measuring device comprising a signal processing unit configured to receive the frequency distribution of the dimensions of the imaged objects; and the signal processing unit is configured to define a measured dimension of an object in the image being a real dimension and modify the frequency distribution of the dimensions of the objects measured from the image by a weighting operation associated with a probability of the real dimensions of the objects being imaged in the image.

19. A measuring device according to claim 18, in which device the signal processing unit is configured to determine the curliness of objects by modifying the dimensions measured from an image and needed for measuring curliness by a weighting operation associated with a probability of the real dimensions of the object being imaged in the image.

20. A measuring device for determining a frequency distribution for a dimension of imaged objects, the measuring device comprising a signal processing unit configured to receive the frequency distribution of the dimension of the objects projected onto the image, the frequency distribution being generated by measuring the dimension of the objects in a space in which the position of each object is at least partly free, the dimension of each object in the image depending on the position of the object and being a real dimension, and the signal processing unit is configured to modify the frequency distribution of the dimension of the projected objects by a weighting operation compensating for the impact of the projection in order to generate a real frequency distribution of the objects.

21. A measuring device according to claim 20, where the signal processing unit is configured to weight the frequency distribution of the dimension of the projected objects by a weighting operation associated with the probability of the positions of the objects.

22. A measuring device according to claim 20, where the signal processing unit is configured to weight the frequency distribution of the dimension of the projected objects by an algorithm serving as a weighting operation, the frequency distribution including categories in which each category in the frequency distribution of the dimension of the projected objects is weighted by means of an inter-category probability associated with the position of the objects.

23. A measuring device according to claim 20, in which, when the frequency distribution of the dimension of the projected objects includes categories, the signal processing unit is configured to weight each category by adding portions thereto, according to a function compensating for the impact of the projection, from other categories representing a smaller dimension, in which the categories are processed in order from a category representing the largest dimension to a category representing the smallest dimension.

24. A measuring device according to claim 20, in which, when the frequency distribution of the dimension of the projected objects includes categories, the signal processing unit is configured to weight each category by adding thereto, according to a function compensating for the impact of the projection, numbers of objects from other categories representing a smaller dimension, in which the categories are processed in order from a category representing the largest dimension to a category representing the smallest dimension.

25. A measuring device according to claim 20, in which the signal processing unit is further configured to determine a dimension for objects imaged in the margin of an image, the objects being partly outside the image, by means of a probability function modifying the measured dimensions.

26. A measuring device for determining a frequency distribution for a dimension of imaged objects, the measuring device comprising a signal processing unit configured to receive the frequency distribution of objects determined from the image, in which image some of the objects are entirely imaged and some of the objects are partly imaged, and the signal processing unit is configured to define a measured dimension of an object in the image being a real dimension, and modify the frequency distribution of the dimensions of the objects measured from the image by a correction operation associated with the dimensions of the image, the dimensions of the objects in the image, and the location of the objects in the image.

27. A measuring device for determining a frequency distribution for dimensions of objects, the measuring device comprising a signal processing means configured to receive the frequency distribution of the dimensions of imaged objects; and the signal processing means is configured to define a measured dimension of an object in the image being a real dimension, and modify the frequency distribution of the dimensions of the objects measured from the image by a weighting operation associated with the probability of real dimensions of the objects from being imaged in the image.

28. A measuring device for determining a frequency distribution for a dimension of imaged objects, the measuring device comprising a signal processing means configured to receive the frequency distribution of the dimension of the objects projected onto the image, the distribution being generated by measuring the dimension of the objects in a space in which the position of each object is at least partly free, the dimension of each object in the image depending on the position of the object and being a real dimension; and the signal processing means is configured to modify the frequency distribution of the dimension of the projected objects by a weighting operation compensating for the impact of the projection in order to generate a real frequency distribution of the objects.

29. A measuring device for determining a frequency distribution for a dimension of imaged objects, the measuring device comprising a signal processing means configured to receive the frequency distribution of the dimensions of objects determined from the image, in which image some of the objects are entirely imaged and some of the objects are partly imaged, and the signal processing means is configured to define a measured dimension of an object in the image being a real dimension, and modify the frequency distribution of the dimensions of the objects measured from the image by a correction operation associated with the dimensions of the image, the dimensions of the objects in the image, and the location of the objects in the image.

* * * * *